United States Patent [19]

Eriksson et al.

[11] Patent Number: 5,461,911
[45] Date of Patent: Oct. 31, 1995

[54] FLOW TRANSDUCER MUFF

[75] Inventors: Sture Eriksson, Vallentuna; Rolf Edstroem, Bromma, both of Sweden

[73] Assignee: Siemens Elema AB, Solna, Sweden

[21] Appl. No.: 210,466

[22] Filed: Mar. 21, 1994

[30] Foreign Application Priority Data

Apr. 22, 1993 [SE] Sweden .................................. 9301345

[51] Int. Cl.⁶ .................................................. G01F 15/14
[52] U.S. Cl. ................................................................ 73/201
[58] Field of Search ........................... 73/118.2, 198, 73/201, 273, 866.5, 201; 248/904; 285/93

[56] References Cited

U.S. PATENT DOCUMENTS 5,020,894  6/1991  Weyrauch et al. ........................ 350/587

FOREIGN PATENT DOCUMENTS 2403304  8/1975  Germany .
4034176  11/1991  Germany .
0048517  5/1981  Japan ........................................ 73/201

OTHER PUBLICATIONS

"Operating Manual for the Servo Ventilator 900C sold by Siemens Elema AB", Aug. 1985, pp. 10:1–10:6.

*Primary Examiner*—Robert Raevis
*Attorney, Agent, or Firm*—Hill, Steadman & Simpson

[57] ABSTRACT

A flow transducer muff for positioning a substantially right-angled parallelepiped-shaped flow transducer in the expiration channel of a ventilator includes a first muff half and a second muff half respectively connectable to opposite sides of the flow transducer, and a connecting link attaching the muff halves together and permitting the muff halves to be bent around the connecting link to fit against the flow transducer.

6 Claims, 1 Drawing Sheet

FLOW TRANSDUCER MUFF

BACKGROUND OF THE INVENTION

1. Field of the Invention

The present invention is directed to a flow transducer muff for positioning a substantially right-angled parallelepiped-shaped flow transducer in the expiration channel of a ventilator, of the type having first and second muff halves which are connectable on opposite sides of the flow transducer.

2. Description of the Prior Art

Expired gas flow is measured in a flow transducer at the expiration side of a ventilator. The flow transducer is maintained in position in the expiration channel by means of a flow transducer muff, which forms a gas-tight connection to the flow transducer. Such a flow transducer muff is described, for example, in the Operating Manual (page 10: 2–3, August 1988) for the Servo Ventilator 900C, sold by Siemens-Elema AB. In general, known flow transducer muffs consist of two halves which are connected on opposite sides of the flow transducer.

The two muff halves in known components are identical in shape, and there is thus a risk that the flow transducer could be installed, after cleaning, in a reversed position in the ventilator.

SUMMARY OF THE INVENTION

It is an object of the present invention to provide a flow transducer muff which assures that the flow transducer is correctly positioned when installed in the expiration channel.

It is a further object of the present invention to provide such a flow transducer muff which is simple to manufacture and which provides a secure, gas-tight connection to the flow transducer, while simultaneously facilitating connection to the flow transducer and reducing the number of components in the expiration channel.

The above objects are achieved in accordance with the principles of the present invention in a flow transducer muff having first muff and second muff halves which are attached to each other by a connecting link, the connecting link permitting the first and second muff halves to be bent around the connecting link to hold the flow transducer between the halves.

The flow transducer muff, with the connecting link, consists of a single (unitary) integrated unit. The connecting link also serves as an orientor for the flow transducer, which ensures that the flow transducer is positioned in the correct direction when introduced into the muff. Because the connecting link is elastically devised, the two muff halves can be readily bent around the connecting link when the flow transducer is to be connected to the flow transducer muff, or disassembled therefrom.

Preferably, the connecting link is formed by a thin, elastic plate having a width which is substantially identical to the diameter of the respective muff halves.

The flow transducer muff constructed in accordance with the principles of the present invention is more stable than conventional muffs because the connecting link has a width which, as noted above, is approximately the same as the diameter of the muff halves.

In order to ensure that the flow transducer is actually positioned in the correct direction within the flow transducer muff, preferably the muff halves are devised with at least one support boss against which at least one end surface of the flow transducer presses, when the flow transducer is attached in the muff.

The boss is shaped and/or positioned so that only the correct orientation of the flow transducer within the muff is permitted. This is achieved because the opening of the flow transducer is not at the center of the flow transducer, so that the presence of the support boss allows the flow transducer to be connected to the flow transducer muff in only one way, i.e., with the correct orientation.

To ensure that the flow transducer muff itself is correctly placed in the expiration channel, preferably the muff halves have an asymmetrical exterior, so that the flow transducer can only be connected in the expiration channel in one way.

The asymmetry of the muff halves can be achieved by providing them with respectively different shapes, or by having respectively different shapes for the connections to other components in the expiration channel.

In a further embodiment of the flow transducer muff of the invention, the muff halves and the connecting link are formed in a single piece, preferably by die-casting.

DESCRIPTION OF THE PREFERRED EMBODIMENTS

Figure 1:
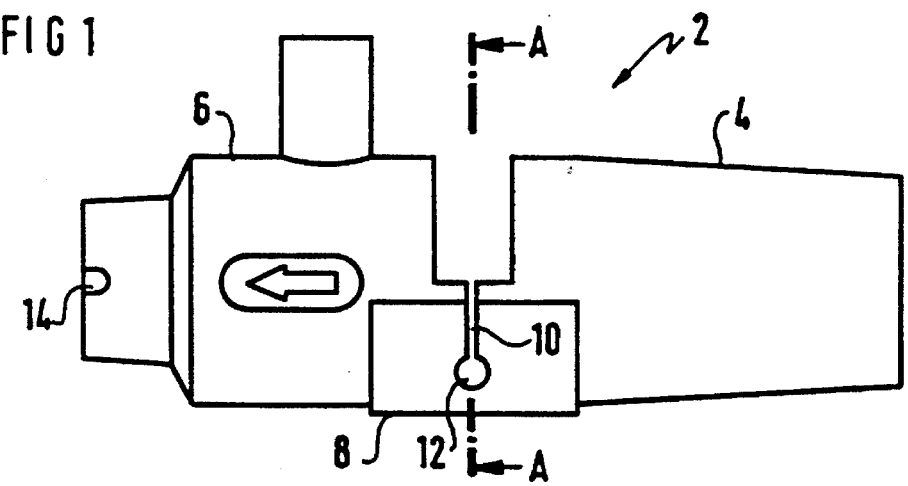
FIG. 1 is a side elevational view of one embodiment of a flow transducer muff constructed in accordance with the principles of the present invention.

The flow transducer muff 2 constructed in accordance with the principles of the present invention and shown in FIG. 1 is die-cast in a single piece, and consists of elastic material. The flow transducer muff 2 is formed essentially of three parts, a first muff half 4, a second muff half 6 and a connecting link 8. The connecting link 8 is provided with a groove 10 which terminates in an open hole 12 to permit the two muff halves 4 and 6 to be bent around the connecting link 8.

To ensure that the flow transducer muff 2 is correctly installed in an expiration channel of a ventilator, the muff halves 4 and 6 have respectively different connection ends. The second muff half 6 has an opening 14 in the end thereof which fits a corresponding part in the expiration channel, so that the flow transducer muff 2 makes a correct fit therewith only with the second muff halve 6 oriented facing this corresponding part.

Figure 2:
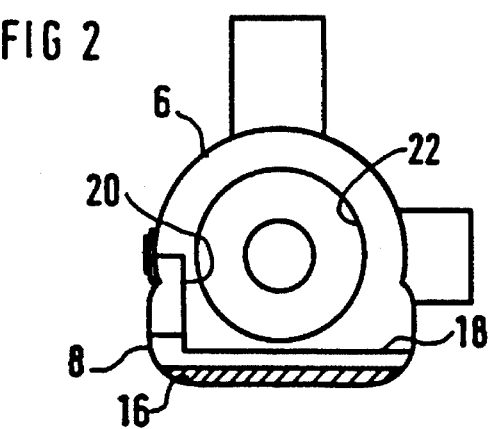
FIG. 2 is a cross-sectional view of the flow transducer muff shown in FIG. 1, taken along line A—A.

FIG. 2 shows a cross-section taken along line A—A of the flow transducer muff 2. In FIG. 2, it can clearly be seen that the connecting link 8 has a thin plate 16 which holds the two muff halves 4 and 6 together.

To ensure that the flow transducer is correctly placed within the flow transducer muff 2, the connecting link 8 has a first support boss 18 and a second support boss 20, against which the flow transducer is pressed when connected to the flow transducer muff 2. Fluid communication with the flow transducer takes place through a connection opening 22 in each muff half 4 and 6 (the opening 22 in the muff half 6 being shown in FIG. 2). The flow transducer is arranged to communicate with the connection opening 22 by means of a corresponding circular shoulder.

Figure 3:
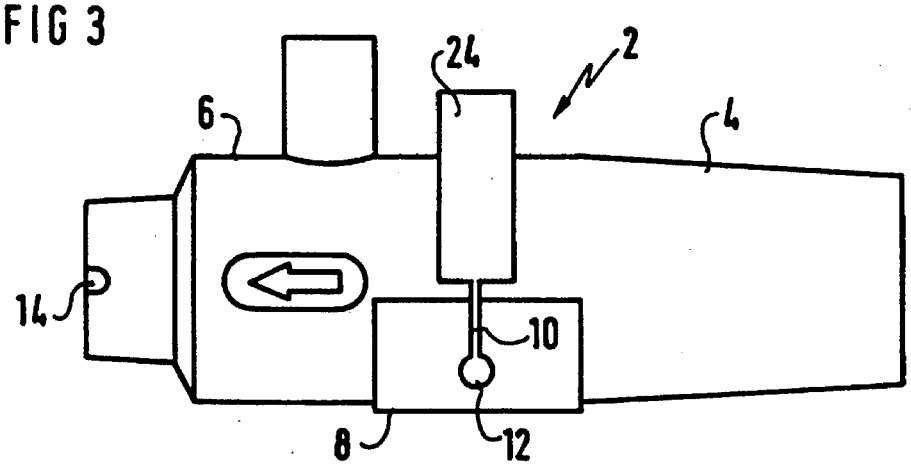
FIG. 3 is a side elevational view of the flow transducer muff of FIG. 1, with a flow transducer connected therein.

The flow transducer muff 2 with a flow transducer 24 connected therein is shown in FIG. 3. Other parts of the flow transducer muff 2 are identical to the parts described in FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A flow transducer muff for positioning a substantially right-angled parallelpiped-shaped flow transducer in an expiration channel of a ventilator, said flow transducer muff comprising:

first and second muff halves each having a gas tight channel therein and respectively shaped to receive a parallelpiped-shaped flow transducer therebetween and comprising means for connecting said channels to opposite sides of said parallelpiped-shaped flow transducer; and an elastic connecting link attaching said first muff half to said second muff half and comprising means for permitting said first and second muff halves to be bent around said connecting link for inserting said parallelpiped-shaped flow transducer between said muff halves and for holding said muff halves against said parallelpiped-shaped flow transducer to produce a substantially gas tight connection between said channels.

2. A flow transducer as claimed in claim 1 wherein said connecting link comprises a thin, elastic plate having a width which is substantially identical to a diameter of said first and second muff halves.

3. A flow transducer muff as claimed in claim 1 wherein said first and second muff halves have at least one support boss, against which at least one end surface of said flow transducer is pressed when said flow transducer is disposed between said first and second muff halves.

4. A flow transducer muff as claimed in claim 1 wherein said first and second muff halves are asymmetrical and comprising means for permitting insertion of said parallelpiped-shaped flow transducer between said muff halves in only one orientation.

5. A flow transducer muff as claimed in claim 1 wherein said muff halves and said connecting link comprise a single, unitary component.

6. A flow transducer muff as claimed in claim 1 wherein said first and second muff halves and said connecting link comprise a single, unitary die-cast component.

* * * * *